(12) United States Patent
Zang et al.

(10) Patent No.: US 8,486,708 B2
(45) Date of Patent: Jul. 16, 2013

(54) PERYLENE NANOFIBER FLUORESCENT SENSOR FOR HIGHLY SENSITIVE AND SELECTIVE SENSING OF AMINES

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 125 days.

(21) Appl. No.: 12/696,952

(22) Filed: Jan. 29, 2010

(65) Prior Publication Data

US 2010/0197039 A1 Aug. 5, 2010

Related U.S. Application Data

(60) Provisional application No. 61/148,780, filed on Jan. 30, 2009.

(51) Int. Cl.
*G01N 21/76* (2006.01)
*C07D 491/052* (2006.01)

(52) U.S. Cl.
USPC ............... 436/111; 436/172; 422/91; 546/37; 977/788

(58) Field of Classification Search
None
See application file for complete search history.

(56) References Cited

U.S. PATENT DOCUMENTS

| | | | |
|---|---|---|---|
| 6,916,982 | B2 | 7/2005 | Loewe et al. |
| 2003/0170904 | A1 | 9/2003 | Hibbert et al. |
| 2009/0233374 | A1 | 9/2009 | Zang et al. |

FOREIGN PATENT DOCUMENTS

| | | |
|---|---|---|
| JP | 9189663 | 7/1997 |
| WO | WO2004/027412 | 4/2004 |
| WO | WO2007/016495 | 2/2007 |

OTHER PUBLICATIONS

Langhals, H. "Control of the Interactions in Multichromophores: Novel Concepts. Perylene Bis-imides as Components for Larger Functional Groups," Helvetica Chimica Acta 2005, 88, 1309-1343.*
Datar, A. "AFM Investigation of 1D Self-Assembly of n-Type Organic Semiconducting Molecules," Master of Science Thesis, Southern Illinois University Carbondale, 2006.*

(Continued)

*Primary Examiner* — Yelena G Gakh
*Assistant Examiner* — Michelle Adams
(74) *Attorney, Agent, or Firm* — Thorpe North & Western LLP

(57) ABSTRACT

A fluorescence sensory material with high sensitivity, selectivity, and photostability has been developed for vapor probing of organic amines. The sensory material is a perylene-3,4,9,10-tetracarboxyl compound having amine binding groups and the following formula

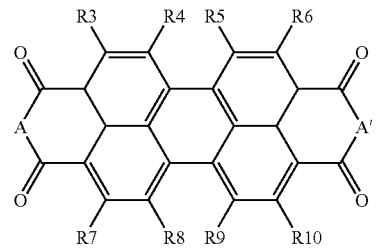

where A and A' are independently chosen from N—R1, N—R2, and O such that both A and A' are not O, and R1 through R10 are amine binding moieties, solubility enhancing groups, or hydrogen such that at least one of R1 through R10 is an amine binding moiety. This perylene compound can optionally be formed into well-defined nanofibers. Upon deposition onto a substrate, the entangled nanofibers form a meshlike, highly porous film, which enables expedient diffusion of gaseous analyte molecules within the film matrix, leading to a milliseconds response for vapor sensing.

23 Claims, 10 Drawing Sheets

OTHER PUBLICATIONS

Online supporting information for Che, Y. et al. "Expedient Vapor Probing of Organic Amines Using Fluorescent Nanofibers Fabricated from an n-Type Organic Semiconductor," J. Am. Chem. Assoc. 2007, 129, 7234-7235.*

Seki, T. et al. "Formation of Supramolecular Polymers and Discrete Dimers of Perylene Bisimide Dyes Based on Melamine-Cyanurates Hydrogen-Bonding Interactions," J. Org. Chem. 2008, 73, 3328-3335; Published on Web Apr. 8, 2008.*

Liu, Y. et al. "Self-Assembly and Characterization of Hydrogen-Bond-Induced Nanostructure Aggregation," ChemPhysChem 2004, 5, 1210-1215.*

Charlet, E. et al. "Ultrathin films of homeotropically aligned columnar liquid crystals on indium tin oxide electrodes," Applied Physics Letters, 92, 024107 (2008), published online Jan. 15, 2008.*

Johnson, E. et al. "Spectroscopic Properties and Packing of Langmuir-Blodgett Monolayers of Perylenetetracarboxylic Anhydrides," Langmuir 1995,11, 1693-1700.*

Che, Y. et al. "Ultralong Nanobelts Self-Assembled from an Asymmetric Perylene Tetracarboxylic Diimide," J. Am. Chem. Soc. 2007, 129, 7234-7235.*

Alibert-Fouet, S. et al. "Electroluminescent Diodes from Complementary Discotic Benzoperylenes," ChemPhysChem 2003, 4, 983-985.*

Brocklehurst, B. et al. "Fluorescence Anisotropy Decays and Viscous Behaviour of 2-Methyltetrahydrofuran," J. Chem. Soc. Faraday Trans. 1994, 90(2), 271-278.*

Che et al., Expedient Vapor Probing of Organic Amines Using Sluorescent Nanofibers Fabricated from an n-Ty;e Organic Semiconductor, Nano Letters, 2008, vol. 8, No. 8, pp. 2219-2223.

Che et al., Ultraselective fluorescent sending of Hg2+ through metal coordination-induced molecular aggregation, Chem. Commun., 2008, pp. 1413-1415.

Mohr, Tailoring the sensitivity and spectral properties of a chromoreactand for the detection of amines and alcohols, Analytica Chimica Acta 508, 2004, pp. 233-237.

Che et al., Enhanced fluorescence sensing of amine vapor based on ultrathin nanofibers, Chem. Commun., 2009, pp. 5106-5108.

Yoshida et al., Fluorescence Sensing Behavior of Thin-films of Benzofuranoquinol Clathrate Host upon Exposure to Various Gaseous Amines, Chemistry Letters 2000, pp. 714-715.

Raible et al., V2O5 nanofibres: novel gas sensors with extremely high sensitivity and selectivity to amines, Sensors and Actuators B 106, 2005, pp. 730-735.

Murray et al., Amine Vapor Sensing with Silver Mesowires, Nano Letters, 2004, vol. 4, No. 4, pp. 665-670.

Oberg et al., Simple optical sensor for amine vapors based on dyed silica microspheres, Sensors and Actuators B 115, 2006, pp. 79-85.

Shanzuo et al., Gas sensing properties of a composite composed of electrospun poly(methyl methacrylate) nanofibers and in situ polymerized polyaniline, Sensors and Actuators B 133, 2008, pp. 644-649.

English et al., Biogenic amine vapour detection using poly(anilineboronic acid) films, Sensors and Actuators B, 2005, pp. 1-6.

Secor et al., Selective Amine Recognition: Development of a Chemosensor for Dopamine and Norepinephrine, Organic Letters, 2004, vol. 6, No. 21, pp. 3727-3730.

Feuster et al., Detection of Amines and Unprotected Amino Acids in Aqueous Conditions by Formation of Highly Fluorescent Iminium Ions, J.Am.Chem.Soc., 2003, 125, pp. 16174-16175.

Charlesworth et al., A Fibre-Optic Fluorescing Sensor for Amine Vapours, http://oai.dtic.mil/oai/oai?verb=getRecord&metadataPrefix=html&identifier=ADA274950, accessed Aug. 31, 2010.

* cited by examiner

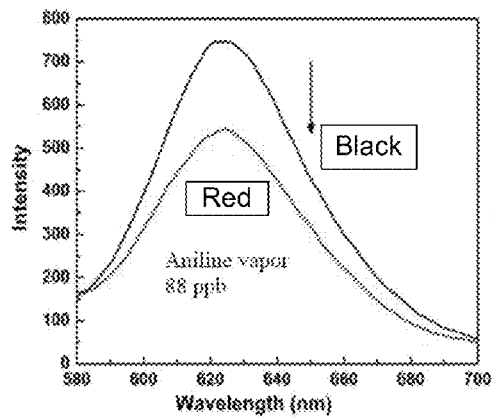
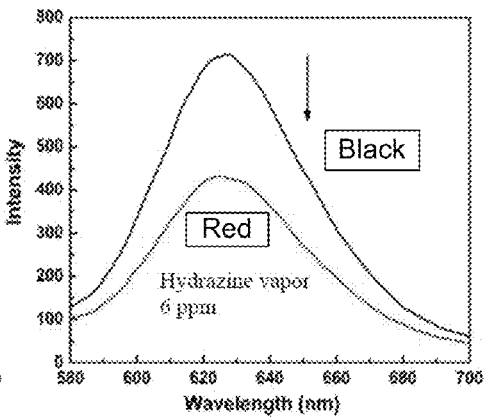
FIG. 7A  FIG. 7B
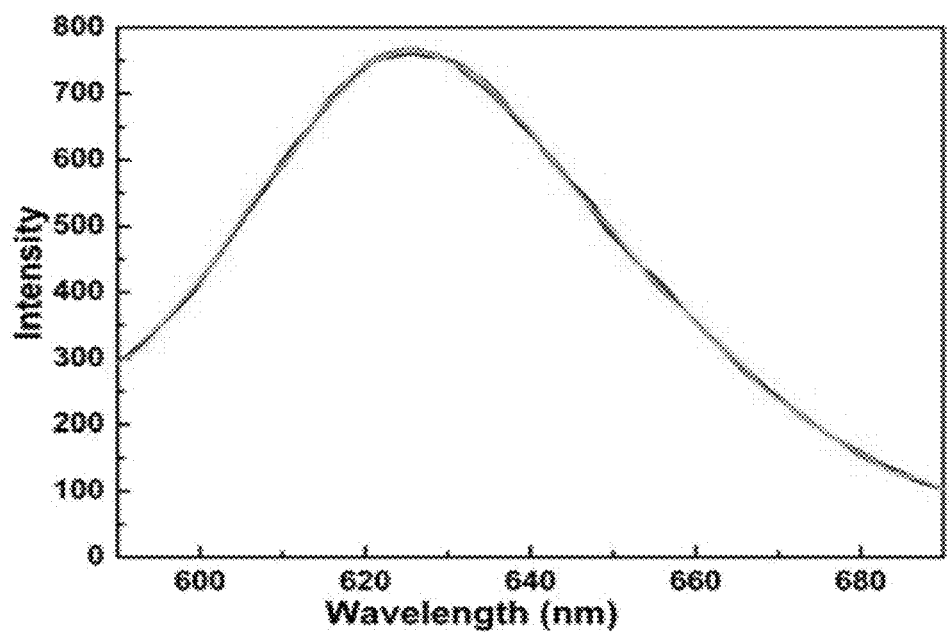
FIG. 8

PERYLENE NANOFIBER FLUORESCENT SENSOR FOR HIGHLY SENSITIVE AND SELECTIVE SENSING OF AMINES

RELATED APPLICATIONS

This application claims the benefit of U.S. Provisional Application 61/148,780, filed Jan. 30, 2009 which is incorporated herein by reference.

GOVERNMENT INTEREST

This invention was made with government support under Grants CHE0641353 and CBET730667 awarded by the National Science Foundation. The Government has certain rights to this invention.

FIELD OF THE INVENTION

This invention relates generally to fluorescent materials, and the use of such materials for detection of amines. Therefore, the present invention relates generally to the fields of chemistry and materials science.

BACKGROUND OF THE INVENTION

Development of sensors or probes that can be used to detect the trace vapor of organic amines represents one of the active research fields in chemistry and materials science, particularly those related to the emerging nanoscience and nanotechnology. Volatile amines have been heavily used in various areas ranging from chemical and pharmaceutical to food industries. Some of the amines, like hydrazine, have also been used in the military as fuel additives in rocket and fighter jet propulsion systems. Detecting these amines with high sensitivity is not only critical to air pollution monitoring and control but also may provide expedient ways for quality control of food and even medical diagnosis of certain types of disease. For example, in diagnosing uremia and lung cancer, released biogenic amines are commonly used as biomarkers.

Although much success has been achieved for detection of amines in solutions using various types of sensors, the vapor-based detection of gaseous amines still remains challenging. This challenge is largely due to the limited availability of sensory materials that enable vapor detection with both high sensitivity and selectivity. Fluorescent sensing and probing based on organic sensory materials represents a unique class of detection techniques that usually provide a simple, expedient way for chemical detection and analysis. However, there are not many organic materials available that are sufficiently fluorescent in the solid state and suited for use as sensory materials in vapor detection. These materials may be strongly fluorescent in molecular state in solutions. Moreover, compared to the more common p-type (i.e., electron donating) materials, which are suited for sensing oxidative reagents like nitro-based compounds, the availability of n-type organic materials (i.e., electron accepting, and suited for sensing reducing reagents like amines) is much more limited.

SUMMARY

In light of the problems and deficiencies noted above, fluorescent sensor compounds for detecting amines can be 3,4,9,10-tetracarboxyl perylene compounds having the formula I:

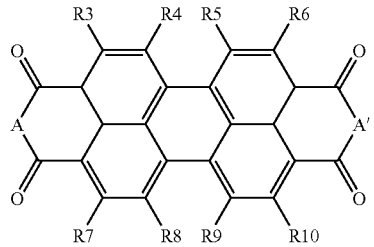

where A and A' are independently chosen from N—R1, N—R2, and O such that both A and A' are not O, and R1 through R10 are amine binding moieties, solubility enhancing groups, or hydrogen such that at least one of R1 through R10 is an amine binding moiety. Typically, the fluorescent sensor compounds can be formed into a nanofiber structure although this is not required.

A nanofiber-based fluorescent sensor compound can be formed via synthesis of the underlying perylene compound which is then formed into the nanofibers. For example, a 3,4,9,10-tetracarboxyl perylene compound having the Formula I (as previously noted) can be synthesized. The perylene compound can be self-assembled into nanofibers via any suitable process such as, but not limited to, a slow controlled solvent-exchange step, rapid solution dispersion, phase transfer at the interface between two solvents, sol-gel processing, direct vaporization of the solvent, or any other suitable self-assembly methods including the surface assisted process. The nanofiber fluorescent sensor compound can optionally be formed into a film of entangled nanofibers by coating the nanofiber dispersion on a substrate.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying figures and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

FIG. 7A is a fluorescence spectra of a nanofibril film before (black) and after (red) exposure to diluted vapor of aniline FIG. 7B is a fluorescence spectra of a nanofibril film before (black) and after (red) exposure to diluted vapor of hydrazine.

FIG. 8 is a fluorescence spectra of a nanofibril film after continuous irradiation at 550 nm for 0, 10, 20, 30, 60 min. The film was held in the LS55 fluorometer with a constant excitation slit of 5 nm and a pulsed Xenon discharge lamp (7.3 W) as the light source. The unchanged fluorescence indicates the robust photostability of the film.

DETAILED DESCRIPTION OF EXEMPLARY EMBODIMENTS

Figure 1:
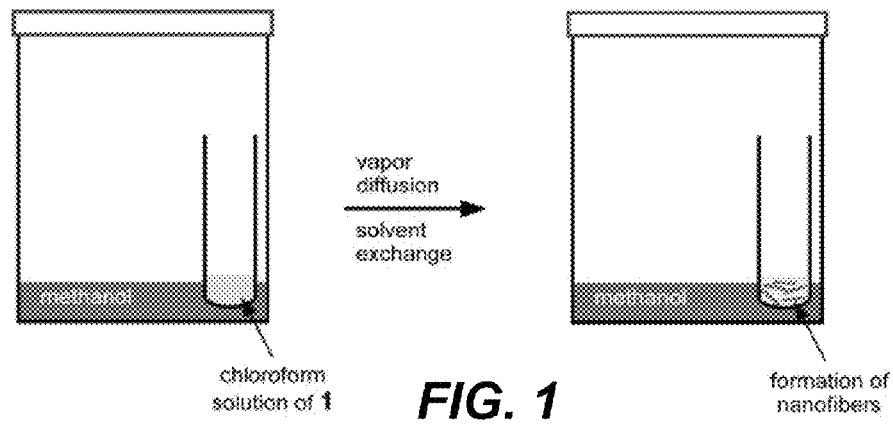
FIG. 1 is a schematic illustration of a slow solvent evaporation system used in accordance with one embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a binding moiety" includes reference to one or more of such groups and reference to "exposing" refers to one or more such steps.

As used herein, "alkylene" refers to a saturated hydrocarbon having two valencies, i.e. for bonding with adjacent groups. Non-limiting examples of alkylenes include —CH—, —CH$_2$—, —C$_2$H$_4$—, —C$_3$H$_6$—, etc. This is in contrast to "alkyl" groups which are similar but have a single valency and include at least one CH$_3$ end group.

As used herein, when referring to a component of a composition, "primarily" indicates that that component is present in a greater amount than any other component of the relevant composition.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims unless clearly indicated otherwise. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Fluorescent Sensor Compounds for Detecting Amines

A new type of fluorescence sensor for expedient vapor detection of organic amines with both high sensitivity and selectivity is provided. The sensing mechanism is primarily based on quenching of the fluorescence emission of the sensory materials upon interaction with the amine molecules. The sensory materials can be composed of well-defined nanofibers fabricated from an n-type organic semiconductor molecule. The long-range exciton migration intrinsic to the one-dimensional well-organized molecular arrangement within the nanofiber enables amplified fluorescence quenching by the surface adsorbed analytes (quencher molecules). Upon deposition onto a substrate, the entangled nanofibers form a mesh-like, highly porous film, which provides maximal adsorption and accumulation of the gaseous molecules under detection, leading to expedient vapor sensing of amines with unprecedented efficiency (down to detection limit in ppt range).

Fluorescent sensor compounds for detecting amines can be 3,4,9,10-tetracarboxyl perylene compounds can generally have the formula I:

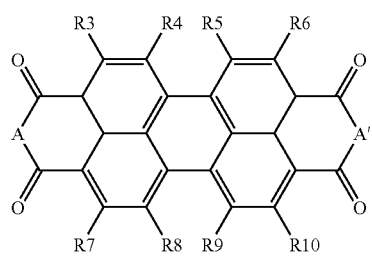

(I)

where A and A' are independently chosen from N—R1, N—R2, and O such that both A and A' are not O, and R1 through R10 are amine binding moieties, solubility enhancing groups, or hydrogen such that at least one of R1 through R10 is an amine binding moiety. Typically, the fluorescent sensor compounds can be formed into a nanofiber structure although this is not required.

In one specific aspect, the fluorescent sensor compound can be an imide-anhydride perylene where A is N—R1 and A' is O. Formula II illustrates one specific class of imide-anhydride perylenes where R3-R6 and R7-R10 are hydrogen.

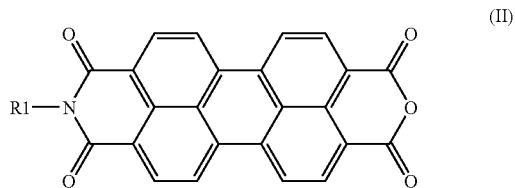

(II)

In this case, the anhydride moiety (O=C—O—C=O) is an amine binding moiety which does not have steric hindrance sufficient to disrupt formation of one-dimensional self-assembly of the compound into a nanofibril structure of the present invention. The group R1 can be chosen to provide solubility of the compound in the organic solvent and which also does not disrupt self-assembly into a nanofibril structure. Such disruption may not be undesirable if nanofibrils are not the intended final product morphology. In one aspect, R1 is a C1 to C13 alkyl chains which can be straight or branched. Non-limiting examples of branched alkyls for R1 can include symmetric branched alkyls such as hexylheptyl, pentylhexyl, and butylpentyl. However, asymmetric branched alkyls can also be suitable such as butylheptyl, 4-methyl-1-hexylheptyl, and the like. As a general rule smaller alkyl chains such as methyethyl and propylbutyl tend to exhibit low solubility, depending on the particular molecule.

In another alternative, the 3,4,9,10-tetracarboxyl perylene compound can be a bisimide, i.e. A is N—R1 and A' is N—R2. Each of R1 and R2 can be C1 to C13 alkyl groups as discussed above. Furthermore, carboxylic acid can be a side group which is added to act as the amine binding group. Formula III illustrates one alternative class of carboxylic acid bisimides of the present invention.

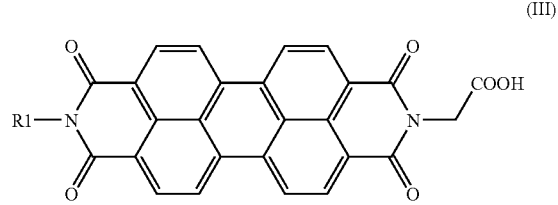

(III)

The solubility enhancing groups can be oriented as side groups (R3-R10) or as in Formula III at R1 to control or increase solubility of the compound during manufacture of nano fibers Although other solubility enhancing groups (R1) can be suitable as outlined herein, one embodiment of formula III can include symmetric alkyl groups such as, but not limited to, hexylheptyl, pentylhexyl, and butylpentyl.

In still another alternative embodiment, the 3,4,9,10-tetracarboxyl perylene compound can include carboxylic acid and/or anhydride moieties. Such side groups can be useful to provide amine binding groups. As discussed in more detailed below, such solution processing usually involves self-assembly mechanisms. In some embodiments, the solubility enhancing moieties can be located along the sides of the perylene core, i.e. R3-R6 and R7-R10. However, most often the amine binding moieties can be located along sides of the perylene core. Formulas IV-VI illustrate several carboxylic acid and anhydride substituted perylene compounds suitable for use in the sensor compounds.

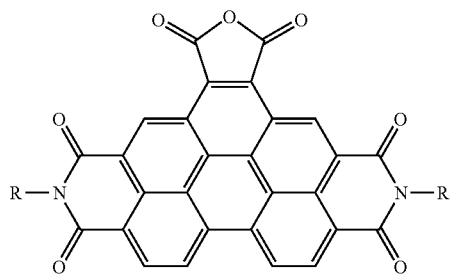

(IV)

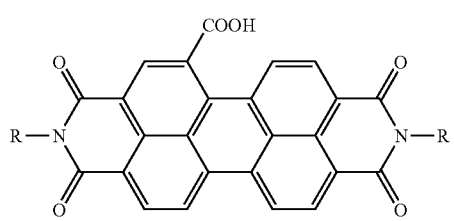

(V)

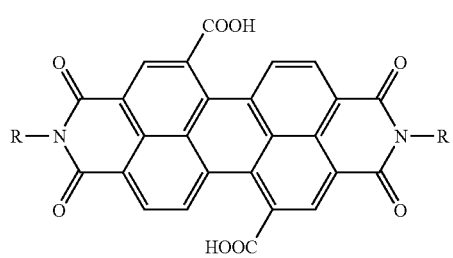

(VI)

Formula IV illustrates a compound having a maleic anhydride moiety formed collectively of R4 and R5. Formula V and IV illustrate 3,4,9,10-tetracarboxyl perylene compounds which include carboxylic acids as side groups, although almost any combination or number of R3 through R10 can be COOH, one or two carboxylic acid groups are most typical. The R1 and R2 end groups can be chosen from among those previously listed. However, C5-C12 cycloalkyls can also be employed as the side-chains substituted at the imide position (A or A') as the solubility enhancing groups to facilitate solution processing. These cycloalkyl groups are suitable for one-dimensional self-assembly of the molecules into nanofibrils. For example, non-limiting examples of cycloalkyls can include cyclopentyl, cyclohexyl, cycloheptyl, cyclooctyl, and cyclododecyl. Specific examples of amine binding sites can include an oxygen moiety like anhydride or an acid like —COOH. While many of the amine-binding moieties mentioned above can be substituted at the bay area, some of the bulky alkyl groups like the branched ones are generally not suitable for substitution at the bay area when forming nanofibers, since they will distort the pi-pi stacking between the perylene planes mainly due to the increased steric hindrance.

The nanofiber-based fluorescent sensor compounds can be formed via synthesis of the underlying perylene compound which is then formed into the nanofibers. For example, a 3,4,9,10-tetracarboxyl perylene compound having the Formula I (as previously noted) can be synthesized. In one specific example, the starting compound used for synthesizing the sensor molecule, 3,4,9,10-tetracarboxylic perylene dianhydride (Formula I with A and A' both as O, and R3-R10 as hydrogen) can be obtained commercially from many chemical manufacturers including Sigma Aldrich and Fisher Scientific. A diimide compound synthesized from the dianhydride can be subjected to partial hydrolysis to form an anhydride imide such as those described by Formula II above.

The perylene compound can be self-assembled into nanofibers via any suitable process such as, but not limited to, a slow controlled solvent-exchange step, rapid solution dispersion, phase transfer at the interface between two solvents, sol-gel processing, direct vaporization of the solvent, or any other suitable self-assembly methods including the surface assisted process. A more detailed description of some of these options can be found in a recent publication, Ling Zang, *Accounts of Chemical Research*, a special issue in Nanoscience, 41 (2008) 1596-1608, which is incorporated herein by reference. The slow controlled solvent-exchange step can be accomplished by dissolving the compound in a suitable good solvent, e.g. dichloromethane, chloroform, tetrachloromethane, alkanes, etc., which typically have a solubility of at least 0.2 mM and in some cases at least 1 mM concentration for the perylene compound. A solution of the perylene compound can be placed in a closed chamber in proximity to a poor solvent (e.g. some solubility for the perylene compound but generally less than about 1 μM concentration and in some cases less than about 0.01 mM). Poor solvents can vary depending on the particular perylene compound but can often include methanol, ethanol, hexane, heptane, cyclohexane, acetonitrile, etc. Vapor diffusion between the two solvents will gradually decrease the concentration of good solvent in the perylene solution and the solubility of the solution. As a result the perylene compound begins to crystallize slowly into the nanofibers of the present invention. The rate of nanofiber formation can depend on the particular solvents, temperature, etc., but is often about a day to reach equilibrium. The ultrathin nanofibers (20-50 nm in diameter) can be fabricated via a quick crystallization method, e.g. injecting the good solvent solution of perylene monoimide (e.g. 0.3 mL, 3.4 mM) into poor solvent (e.g. hexane, 1.2 mL) in a small test tube, followed by 30 min aging.

The nanofibers can vary in size, depending on the specific perylene compound used. However, as a general guideline, the nanofibers can have a diameter from about 10 nm to about 1000 nm, in some cases to about 500 nm, and one aspect from about 100 nm to about 350 nm while in another aspect from about 10 nm to about 50 nm. Similarly, the length of the nanofibers can vary considerably but is often from about 1 μm to about 1 mm, and in some cases from about 10 μm.

The formed nanofibers can then be suspended in a liquid vehicle in which the nanofibers are very poorly soluble, e.g. less than about 1 micromolar concentration, at least less than 0.01 mM, or completely insoluble, to form a nanofiber dispersion. Non-limiting examples of suitable liquid vehicles can include hexane, heptane, methanol, cyclohexane, alcohols, and the like.

The nanofiber fluorescent sensor compound can be formed into a film of entangled nanofibers by coating the nanofiber dispersion on a substrate and allowing the solvent to evaporate.

The formed nanofibers have shown rapid fluorescence responses upon exposure to various amine compounds. The nanofiber fluorescent sensor compound can be exposed to a fluid sample in which the nanofiber fluorescent sensor compound is not substantially soluble. The fluid sample can generally be a fluid containing the target gaseous analyte, although liquids can also be tested. A fluorescence change can be measured and/or displayed upon exposure of the nanofiber sensor compound to the fluid sample. Typically, the fluorescence change can be accomplished using a fluorometer, or simply a photon detector that can measure the fluorescence emission intensity. Depending on the application, the displaying of fluorescence change can be a quantitative measure of fluorescence response, e.g. a percentage change of luminescence intensity. Alternatively, the displaying is qualitative such as by visual observation of a fluorescence change. Such qualitative measure can be sufficient when the mere presence of a particular amine is sought rather than an absolute measure of the concentration.

The specific performance of individual perylene nanofibers can vary. However, in one aspect of the invention, the nanofiber fluorescent sensor compound can exhibit a fluorescence change (e.g. quenching) from 50% to 100% for a majority of amines selected from the group consisting of phenol, cyclohexylamine, dibutylamine, aniline, butylamine, triethylamine, hydrazine, and ammonium hydroxide. Furthermore, the fluorescence change for each of cyclohexylamine, dibutylamine, aniline, butylamine, triethylamine, hydrazine, and ammonium hydroxide can most often be from about 80% to about 100%.

Advantageously, the nanofiber fluorescent sensor compounds can be regenerated by dissolving the nanofiber fluorescent sensor compound and regenerating the nano fibers as previously described. It is noted that such regeneration also does not typically involve a chemical reaction, but rather dissolving of the perylene compound in a suitable solvent and repeating the self-assembly process previously described. Thus, although not generally regenerable by an end user, the sensor compound can be readily collected and recycled with no residual effects on the performance of the material.

Furthermore, the fluorescent sensor compounds can be used as fluorescent dyes or other applications such as in solar cells and the like which do not require nanofiber morphology. This technology can also find a broad range of applications in health and security examination, where instant detection of trace amine is usually demanded. Indeed, sensitive vapor detection of organic amines is not only critical to the air pollution monitoring and control, but will also provide expedient ways for food quality control, and even medical diagnosis of certain types of disease, e.g., uremia and lung cancer, for which biogenic amines released are usually used as the biomarkers.

Compared to the electrical sensors like those based on chemiresistors, the reported fluorescent (optical) sensor system represents a class of simple, expedient technique for chemical vapor detection and analysis. In contrast to the polymer film-based fluorescent sensors, the nanofibril film-based sensors provide three-dimensional continuous pores (or channels) formed by the entangled piling of the nanofibers, enabling expedient diffusion of the analyte molecules throughout the film matrix, and thus fast response (milliseconds) for the sensing. The high porosity (and thus large surface area) formed by the entangled piling of nanofibers also provides maximal adsorption and accumulation of the gaseous molecules under detection, leading to expedient vapor sensing of amines with unprecedented efficiency (down to detection limit in ppt range). The nanofibril materials, as well as the new sensing module thus developed, can open wide options to improve the detection efficacy and find broad range of applications in health and security examination, where instant detection of trace amine is usually demanded.

PTCDI (perylene-tetracarboxylic diimide) represents a robust class of n-type organic materials with strong photostability, which is particularly desirable for being used in optical sensing or probing regarding both the performance sustainability and reproducibility. The sensor compounds can find broad applications in health and security examination. For example, air quality and security industries can benefit from real time amine detection. In-field monitoring of air quality against pollution by toxic amines is one example, which have commonly been used in various industry and military systems. Particularly, hydrazine has been heavily used in both industry (as an oxygen scavenger and corrosion inhibitor) and military (as a fuel in rocket propulsion systems). Moreover, this compound has been implicated as a carcinogen and is readily absorbed through the skin. Another typical toxic amine is ethanolamine, which has been used as the scrubbing agent in the ventilation system of submarines to remove carbon dioxide from the air. Due to their toxicity and reactivity, facile detection of these amines is relevant to both life and environment security.

Health and clinic applications can include rapid screening of uremia and lung cancer, one of the most common cancers, particularly in the developing countries. Alkyl-amines will be used as the biomarkers for uremia diseases, while aromatic-amines will be used for lung cancer. Very trace amount of amines breathed out of the patient will be detected (at concentration of ppt), thus enabling rapid diagnostics or warning of the diseases at the early stage. Food industry applications can include high throughput quality control and monitoring by detecting the amines released from foods.

A new type of fluorescence sensory material with high sensitivity, selectivity, and photostability has been developed for vapor detection of organic amines. The sensory material is primarily based on well-defined nanofibers fabricated from an n-type organic semiconductor molecule. Upon deposition onto a substrate, these entangled nanofibers form a meshlike, highly porous film, which allows for maximal exposure to the gaseous analyte molecules, expedient diffusion of the molecules throughout the meshlike film, and increased adsorption and accumulation of the gaseous molecules within the porous matrix.

Compared to the electrical sensors like those based on chemiresistors, the reported fluorescent sensor system represents a class of simple, expedient technique for chemical detection and analysis. In contrast to the polymer-film-based fluorescent sensors, the nano fibril-film-based sensors provide three-dimensional continuous pores (or channels) formed by the entangled piling of the nanofibers, enabling expedient diffusion of the analyte molecules throughout the film matrix, and thus fast response (milliseconds) for the sensing. The nanofibril materials, as well as the new sensing module thus developed, may open wide options to improve the detection efficacy and find broad range of applications in health and security examination, where instant detection of trace amine is highly beneficial.

Example 1

A strongly fluorescent n-type organic semiconductor material, which can be fabricated into well-defined nanofibers and employed in efficient fluorescent probing of gaseous amines is described. Without being bound to any particular theory, it is thought that the long-range exciton migration intrinsic to the one-dimensional well-organized molecular arrangement within the nanofiber enables amplified fluorescence quenching by the surface adsorbed analytes (quencher molecules). Taking advantage of such amplified fluorescence quenching intrinsic to nanofibers, a new type of nanofibers was fabricated from an n-type material that can be used for effective sensing of reductive compounds, such as organic amines, through electron-transfer-based fluorescence quenching. The building block molecule (1) employed for the nanofibril fabrication is shown in Formula V, which was synthesized through partial hydrolysis of hexylheptyl substituted 3,4,9,10-perylene-tetracarboxylic diimide (PTCDI).

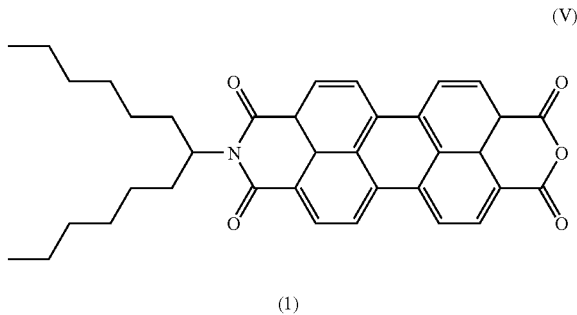 [SMILES: CCCCCCC(CCCCCC)N1C(=O)C2=CC=c3c4c(c5c6c3=CC=C3C(=O)OC(=O)C(C=C5)C36)C=CC(C1=O)C24]

(V)

(1)

In particular, N-(1-hexylheptyl)perylene-3,4,9,10-tetracarboxyl-3,4-anhydride-9,10-imide (1) was synthesized by suspending 1 g N,N'-di(hexylheptyl)-perylene-3,4,9,10-tetracarboxyl-diimide (1.3 mmol) in 60 mL of t-BuOH containing 700 mg solid KOH (85%). The mixture was heated with vigorous stirring to reflux. After refluxing for 1.5 h, the reaction solution was cooled to room temperature, followed by addition of 50 mL of 2 M HCl, followed by stirring over night. The resulting solid was collected by vacuum filtration through a 0.45 μm membrane filter (Osmonics). The solid was then washed thoroughly with distilled water until the pH of washings turned to be neutral. The hydrolyzed product from N,N'-di(hexylheptyl)-perylene-3,4,9,10-tetracarboxyl-diimide was directly purified by column chromatography (eluent: methylene chloride), yielding 0.35 g (35%) of molecule 1, having the following properties: $^1$H-NMR (CDCl$_3$): δ=0.83 (t, 6H, 2CH$_3$), 1.17-1.42 (m, 16H, 8CH$_2$), 1.85 (m, 2H, CH$_2$), 2.24 (m, 2H, CH$_2$), 5.19 (m, 1H, CH), 8.67 (m, 8H, perylene).

Self-assembly of molecule 1 into nanofibers was performed through a slow solvent-exchange process, which was realized via vapor diffusion within a closed chamber. Briefly, a test tube containing about 0.2 mL CHCl$_3$ solution of 1 (1.7 mM) was placed in a 50 mL jar, which contained about 10 mL of methanol, followed by sealing the jar for slow vapor diffusion between the two solvents (FIG. 1). Upon gradual solvent exchange, the solution in the test tube became more dominant with methanol, which is a poor solvent (with low solubility) for molecule 1, thereby leading to self-assembly of the molecules into nanofibers.

Because of the slow crystallization process controlled by the slow vapor diffusion, the nanofibers fabricated via such a process are usually in a well-defined shape and sizes as shown in FIG. 2A-D. After about one day the exchange between the two solvents reached the equilibrium, resulting in complete assembly of the molecules, and precipitating down to the bottom of the test tube. The nanofibers thus obtained were re-dispersed in hexane, producing a suspension well-suited for deposition on a substrate either for microscopy imaging or vapor sensing tests. For each of the sensing tests, the whole amount of the nanofibers thus prepared were deposited on a glass substrate to produce a film that maintained the same surface area (adsorption) for all the sensing tests as presented in FIG. 3A.

The fluorescence quantum yield (φ) of the nanofibril film was estimated by measuring the absorption and fluorescence intensity in comparison with a thin-film fluorescence standard with φ=100%. The thin-film standard was prepared by sandwiching one drop of a polystyrene/toluene gel between two glass cover slips. Within the gel was dissolved an appropriate concentration of a PTCDI molecule, N,N'-di(hexylheptyl)-perylene-3,4,9,10-tetracarboxyl-diimide (HH-PTCDI). By maintaining molecular dispersion of the molecules within the gel, the fluorescent quantum yield of HH-PTCDI remains 100%, as it is dissolved in a homogeneous solution in toluene or other good organic solvents.

Figure 2:
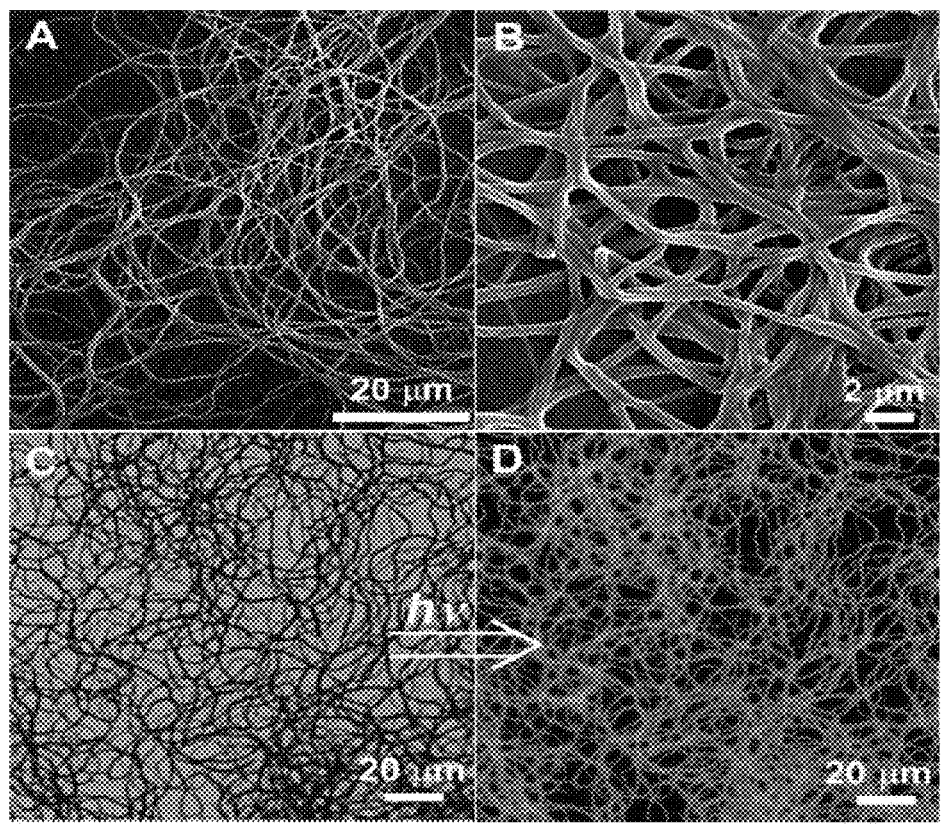
FIG. 2 shows (A) SEM image of a nanofibril film deposited on a glass slide. (B) Zoom-in SEM image of the nanofibril film. (C, D) Bright-field and fluorescence optical microscopy image of a nanofibril film. Note that due to the diffraction effect the fiber in the optical microscopy image appears larger than the real size as measured by SEM.

Molecule 1 possesses a structure that provides a good balance between the molecular stacking and the fluorescence yield of the materials thus assembled. The former prefers a molecular structure with minimal steric hindrance (usually referring to a small or linear side chain), while the latter favors bulky, branched side chains that may distort the π-π stacking to afford increased fluorescence (by enhancing the low-energy excitonic transition) for the molecular assembly. FIG. 2A shows the scanning electron microscopy (SEM) image of the nanofibers fabricated from molecule 1 through the vapor-diffusion (slow solvent exchange) process as described in FIG. 1. The average diameter of the nanofibers was ~350 nm as determined by zoom-in SEM imaging as shown in FIG. 2B.

The extended one-dimensional molecular arrangement obtained for molecule 1 is likely dominated by the π-π interaction between the perylene backbones (which is sterically favored by the bare end of molecule 1), in cooperation with the hydrophobic interactions between the side chains in appropriate size. Such a molecular arrangement is reminiscent of the one-dimensional self-assembly commonly observed for detergents, lipids, or amphiphilic peptides, for which extended molecular assembly can be achieved through the concerted electrostatic and hydrophobic interactions. It seems that one-dimensional molecular assembly of molecule 1 is dependent on the size of the side chains. Replacing the side chain of molecule 1 with a larger group, for example, nonyldecyl, resulted in formation of only ill-shaped molecular aggregates. The nanofibers fabricated from molecule 1 demonstrates strong fluorescence with yield 15% as depicted in the fluorescence microscopy images (FIG. 2C and FIG. 2D), implying a distorted molecular stacking that is usually observed for the PTCDI molecules modified with branched side chains. The strong red fluorescence of the nanofibers can easily be observed even with the naked eye, making the nanofibers more feasible to be used in qualitative fluorescence sensing. Although not essential to an understanding of the compounds, an illustrative movie clip shows a demonstration of one embodiment of this compound and can be found at pubs.acs.org (Supporting Information for Nano Lett., 2008, 8(8), 2219-2223, which article is incorporated herein by reference) or www.chem.siu.edu/zang/image/gas-sensor.wmv.

Figure 3A:
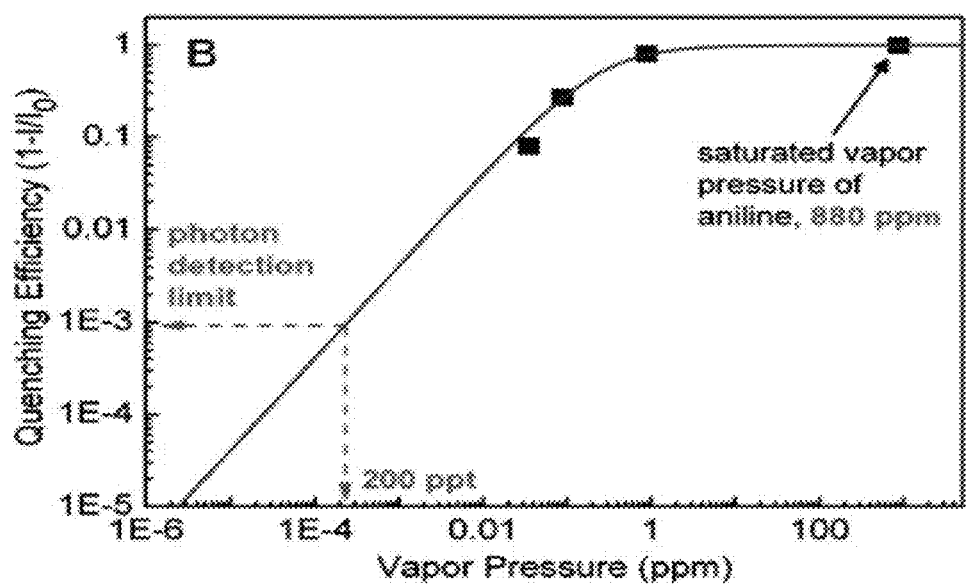
FIG. 3A is a fluorescence quenching efficiency $(1-I/I_0)$ as a function of the vapor pressure of aniline: data (error 5%) fitted with the Langmuir equation.
Figure 3B:
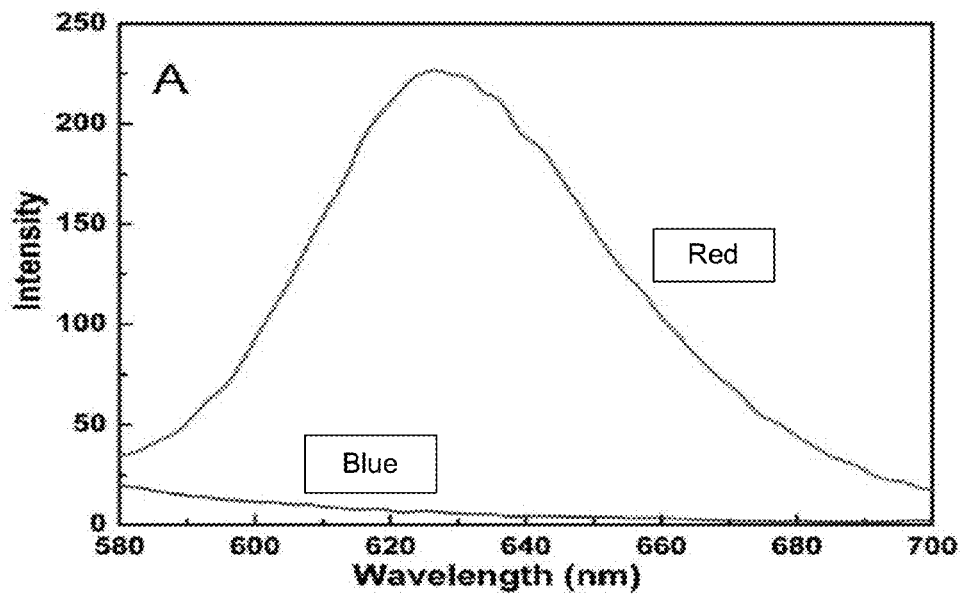
FIG. 3B is a fluorescence spectra of a nanofibril film before (red) and after (blue) exposure to the saturated vapor of aniline (880 ppm) for 10 s.
Figure 3C:
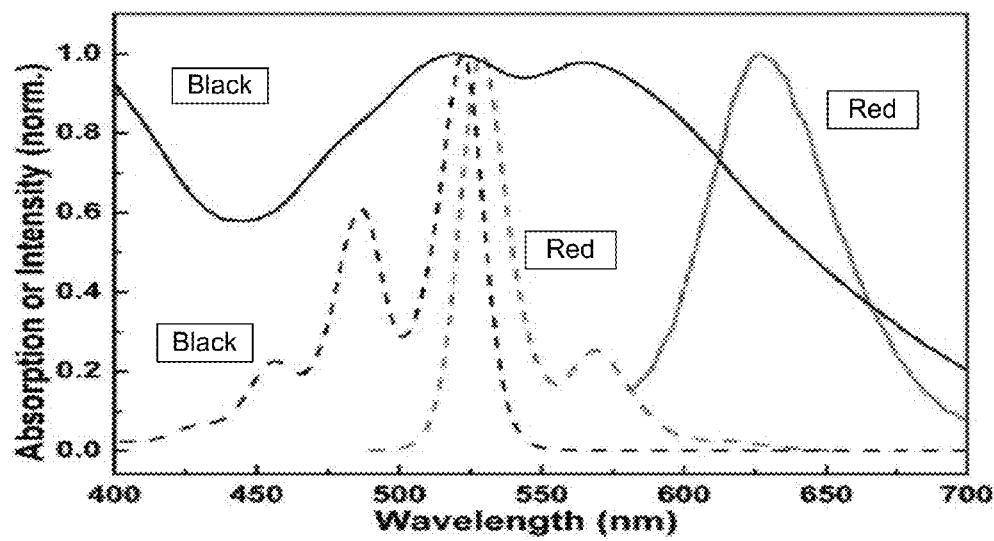
FIG. 3C shows the absorption (black) and fluorescence (red) spectra of molecule 1 in chloroform solution (dashed) and the nanofiber state (solid). The raised baseline for the absorption spectrum of nanofibril film is primarily due to the light scattering.
Figure 4:
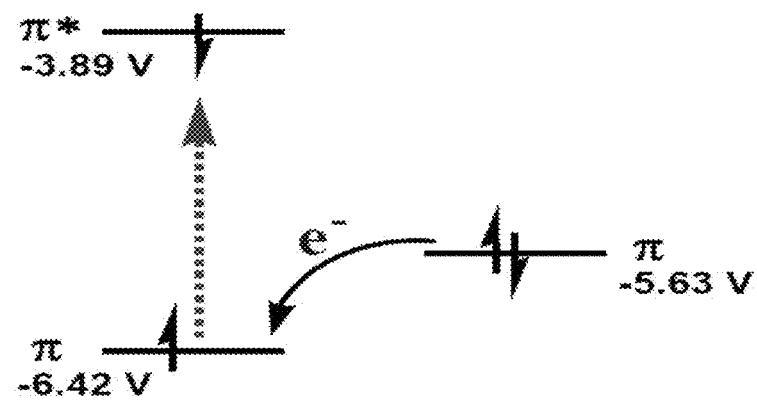
FIG. 4 shows energy levels of HOMO ($\pi$) and LUMO ($\pi^*$) orbitals of 1 and aniline showing the favorable electron transfer from amine to the photoexcited state of 1. The same diagram applies to the other amines, while the reducing power (or the $\pi$-orbital level) would be different from that of aniline (see Table 1). Geometry optimization and energy calculation were performed with density-functional theory (B3LYP/6-311g**//B3LYP/6-31g*) using Gaussian 03 package.

FIG. 3C shows the absorption and fluorescence spectra measured from the nanofibers deposited on glass substrate, in comparison to the spectra measured for molecule 1 dissolved in a chloroform solution. The electronic property of molecule 1 as depicted in FIG. 3C is quite similar to the parent PTCDI molecules with the HOMO-LUMO gap around 2.5 eV, consistent with the ab initio calculation results (FIG. 4).

TABLE 1

Physical properties and quenching results of various amines and phenol

| Analyte | Oxidation potential[a] $E_{1/2}$ value(V) vs SCE | Driving force[a] $\Delta G$ (-eV) | Vapor pressure[b] ppm at 25° C. | Quenching efficiency (10 s of exposure) (%) |
|---|---|---|---|---|
| Butylamine | 1.52 | 0.62 | 120400 | 96 |
| Pentylamine | 1.69[c] | 0.45 | 39480 | 95 |
| Hexylamine | 1.72[d] | 0.42 | 8580 | 95 |
| Octylamine | — | — | 1280 | 94 |
| Dibutylamine | 1.20 | 0.94 | 3360 | 91 |
| Triethylamine | 0.99 | 1.15 | 75990 | 85 |
| Cyclohexylamine | 1.72[d] | 0.42 | 11840 | 94 |
| Cyclopentylamine | — | — | — | 94 |
| Aniline | 0.86 | 1.28 | 880 | 95 |
| Hydrazine | 0.43 | 1.71 | 5920 | 98 |
| Phenol | 1.37 | 0.77 | 340 | 54 |

[a]The driving force for the fluorescence quenching, i.e., photoinduced electron transfer from the analyte to 1 was calculated using the Rehm-Weller equation: $\Delta G = -e(E^\circ_{red} - E^\circ_{ox}) - \Delta E_{oo}$, where $E^\circ_{red}$ and $E^\circ_{ox}$ are the reduction potential of electron acceptor and the oxidation potential of electron donor, respectively, and $\Delta E_{oo}$ is the singlet excitation energy.
[b]The vapor pressure data are cited from CRC handbook of Chemistry and Physics, 85th Edition, CRC Press, 2004, p15-16 to 25.
[c]The oxidation potential of pentylamine (determined as the peak potential).
[d]The oxidation potentials of hexylamine and cyclohexylamine. The relatively lower quenching efficiency observed for the tertiary amines might be due to the weaker chemical binding with the anhydride, with which the binding of a tertiary amine is primarily through the donor-acceptor interaction, but lack of hydrogen bonding.

Figure 5:
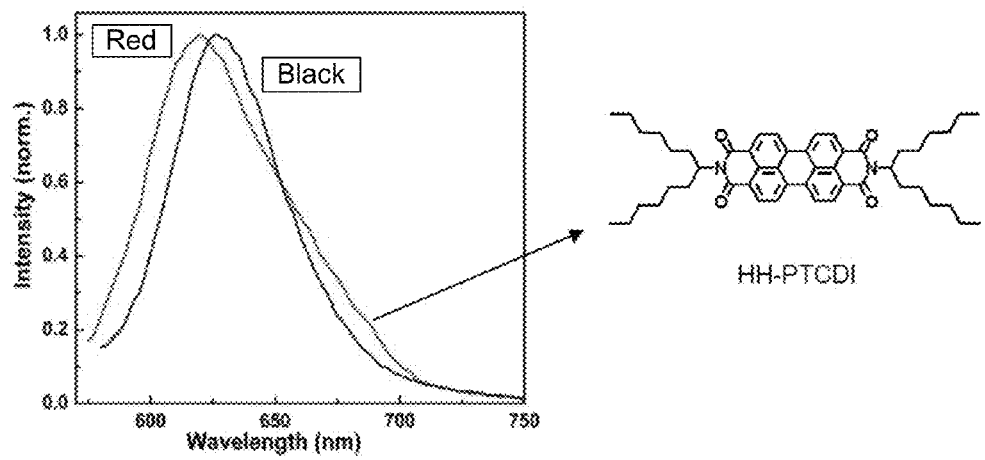
FIG. 5 is a comparison between the fluorescence spectra of the nanofibril film of 1 (black) and a thin film (red) drop-cast from the THF solutions of a PTCDI molecule modified by two bulky, branched side-chains, N,N'-di(hexylheptyl)-perylene-3,4,9,10-tetracarboxyl-diimide (HH-PTCDI), which forms ill-shaped aggregates, mainly due to the significant steric hindrance caused by the large side-chains.

The fluorescence quantum yield of molecule 1 in solution is ~100%, the same as other PTCDI molecules tested. Upon assembly into the solid state, the fluorescence of individual molecules disappeared, while a new emission band formed at a longer wavelength centered around 628 nm. Compared to the emission spectrum (0.21 eV fwhm) obtained from the ill-shaped molecular aggregate formed from the parent PTCDI molecule modified with two hexylheptyl side chains (FIG. 5), the emission measured for the nanofibers of molecule 1 exhibits a significantly narrower band, only 0.17 eV fwhm, implying the well-organized molecular assembly within the nanofibers. Consistently, a new, pronounced band was observed at the longer wavelength in the absorption spectrum of the nanofibers, which is typically characteristic of the strong π-π interaction as observed in the self-assemblies of PTCDI and other planar π-conjugated molecules. The strong π-π interaction is also revealed by the characteristic enhancement of the transitions (absorptions) from ground state to the higher levels of electronic states (0-1, 0-2, and 0-3, compared to 0-0) of the component molecules. The strong π-π interaction may enhance the exciton migration, which is now more confined along the long axis of the nanofiber, leading to amplification in fluorescence quenching by the surface adsorbed analytes (quenchers).

Upon fabrication from hydrophilic solvents such as alcohols, the nanofibers are expected to possess a surface predominantly consisting of the anhydride moieties, which are more hydrophilic compared to the hexylheptyl group located at the other end of the molecule. A surface full of anhydride moieties enables strong chemical binding or adsorption with amines through both hydrogen bonding and donor-acceptor (charge transfer) interaction. Deposition of the nanofibers onto a substrate produces a meshlike film that is primarily formed by entangled piling of the fibers and thus possesses porosity on a number of length scales (FIG. 2A-D). Such a porous film not only provides increased surface area for enhanced adsorption of gaseous molecules but also enables expedient diffusion of guest molecules across the film matrix, leading to efficient probing of the gaseous molecules with both high sensitivity and fast time response.

The organic compounds employed for sensing tests include methanol, acetone, acetic acid, THF, acetonitrile, chloroform, toluene, hexane, cyclohexane, nitrobenzene, nitromethane, phenol, cyclohexylamine, bibutylamine, aniline, butylamine, triethylamine, hydrazine, and ammonium hydroxide. All the compounds and/or solvents (HPLC or spectroscopic grade) were purchased from Fisher or Aldrich, and used as received.

UV-vis absorption and fluorescence spectra were measured on a PerkinElmer Lambda 25 spectrophotometer and LS 55 fluorometer, respectively. SEM measurement was performed with a Hitachi S570 microscope (operated at 10 kV). The sample was prepared by casting one drop of the nanofiber suspension in hexane onto a clean glass cover slip, followed by drying in air and then annealing overnight in an oven at 45° C. The dried sample was coated with gold prior to the SEM imaging. The bright-field optical and fluorescence microscopy imaging was carried out with a Leica DMI4000B inverted microscope, using a Rhodamine filter set, which provides excitation in the range of 530-560 nm, and collects emission at >580 nm.

The fluorescence quenching by amines vapor was monitored. Briefly, the fluorescence spectra of the film were measured immediately after immersing inside a sealed-jar (50 mL) containing small amount of the amines. To prevent direct contact of the film with the amines, some cotton was placed above the amines (deposited at the bottom of the jar). Before use the jar was sealed for overnight to achieve saturated vapor inside. The presence of cotton also helps maintain a constant vapor pressure. The fluorescence quenching at the diluted vapor pressures of amines (e.g., aniline and hydrazine) was performed in a sealed cuvette (5 mL volume), into which a small volume of the saturated vapor of a specific amine was injected (using an air-tight micro-syringe) to achieve the diluted vapor. For example, injection of 5 μL of saturated aniline vapor (880 ppm) into the 5 mL cuvette will produce a vapor pressure 1000 times diluted, e.g., 880 ppb. The lowest vapor pressure of aniline that can be achieved through vapor dilution was about 35 ppb, for which two steps of dilution were carried out, i.e., 50 μL of the ambient saturated vapor of aniline was injected into a 5 mL jar immersed in a water bath (ca. 70° C., to avoid minimal condensation of the vapor), followed by injecting 20 μL of this diluted vapor into the 5 mL cuvette.

The time-dependent fluorescence quenching profile (shown in FIG. 6) was measured with an Ocean Optics USB4000 fluorometer, which can be switched to the mode to measure the emission intensity at a selected wavelength as a function of time. An open sample holder (Ocean Optics, CUV-ALL-UV) was used to hold the nanofibril film deposited on a glass cover slip, and the fluorescence from the nanofibers was collected at 90° with respect to the excitation beam, which was provided by an $Ar^+$ laser (Melles Griot) tuned at 488 nm. Both the excitation and emission were transported with 0.6 mm premium UV/Vis fibers (Ocean Optics). The fluorescence quenching was carried out by blowing a few mL of saturated aniline vapor (880 ppm) onto the nanofibril film during the course when the emission was continuously recorded by the fluorometer.

Figure 6:
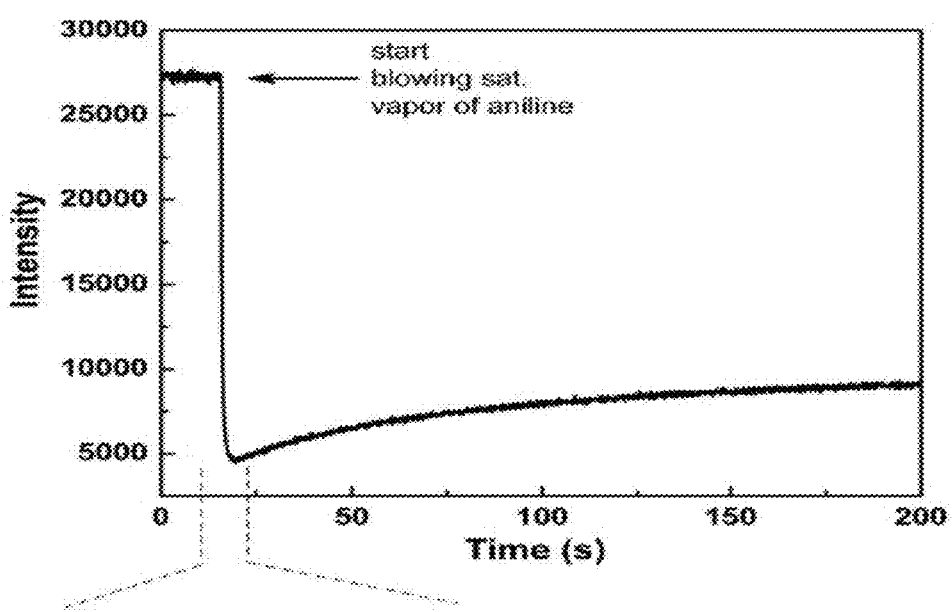
FIG. 6 is a time-course of fluorescence quenching of a nanofibril film upon blowing over with saturated vapor of aniline (880 ppm), indicating a response time of about 0.32 s. The intensity was monitored at 628 nm.

Indeed, as shown in FIG. 6, upon exposure to the saturated vapor of aniline (880 ppm) the fluorescence of the nanofibril film was instantaneously quenched by almost 100%. Such efficient fluorescent sensing was also observed for a broad range of amines (primary, secondary, and tertiary) as listed in Table 1 above. The fluorescence quenching thus observed is due to a photoinduced electron transfer process as depicted in FIG. 4 where the electron transfer is driven by the favorable energy difference between the HOMO of aniline and the HOMO of PTCDI (which is now one electron vacant in the excited state). The high efficiency of the fluorescence quenching is consistent with the large driving force for the photoinduced electron transfer between the excited state of molecule 1 and the amine molecules (FIG. 4 and Table 1).

To explore the detection limit for some of the representative amines such as aniline and hydrazine, the same quenching process shown in FIG. 3B was also examined for the diluted amine vapor. FIG. 3A shows the fluorescence quenching efficiency $(1-I/I_0)$ of a nanofibril film measured at four different vapor pressures of aniline, 1, 1000, 10,000 and 25,000 times diluted from the saturated vapor (880 ppm) at room temperature. The quenching data are well fitted to the Langmuir equation with an assumption that the quenching efficiency is proportional to the surface adsorption (coverage) of amines. From the fitted plot the detection limit of the nanofibril film shown in FIG. 3A can be projected as low as ~200 ppt, if considering the fact that a well-calibrated photodetector (e.g., PMT) can detect intensity change as small as 0.1% or below. Following the same procedure the detection limit for hydrazine was estimated to be ~1 ppb.

FIG. 6 shows the emission intensity of the film monitored as a function of the time after exposed to the saturated vapor of aniline (880 ppm). Fitting the intensity decay into a single exponential kinetics deduces a response time for the quenching process (defined as the decay lifetime), only 0.32 s. The fast response thus obtained for the nanofibril sensor is mainly due to the three-dimensional continuous, porous structure formed by the entangled piling of the nanofibers, which allows for expedient diffusion of the analyte molecules throughout the film matrix, thus leading to instant capture (and accumulation) of the vapor species. The fast sensing response, along with the low detection limits and the robust photostability (zero photobleaching, as shown in FIG. 8) observed, makes the nanofibril film an ideal probing system in a broad range of applications, particularly for onsite amine monitoring and screening, where instant vapor detection of trace amines is usually demanded.

Figure 9:
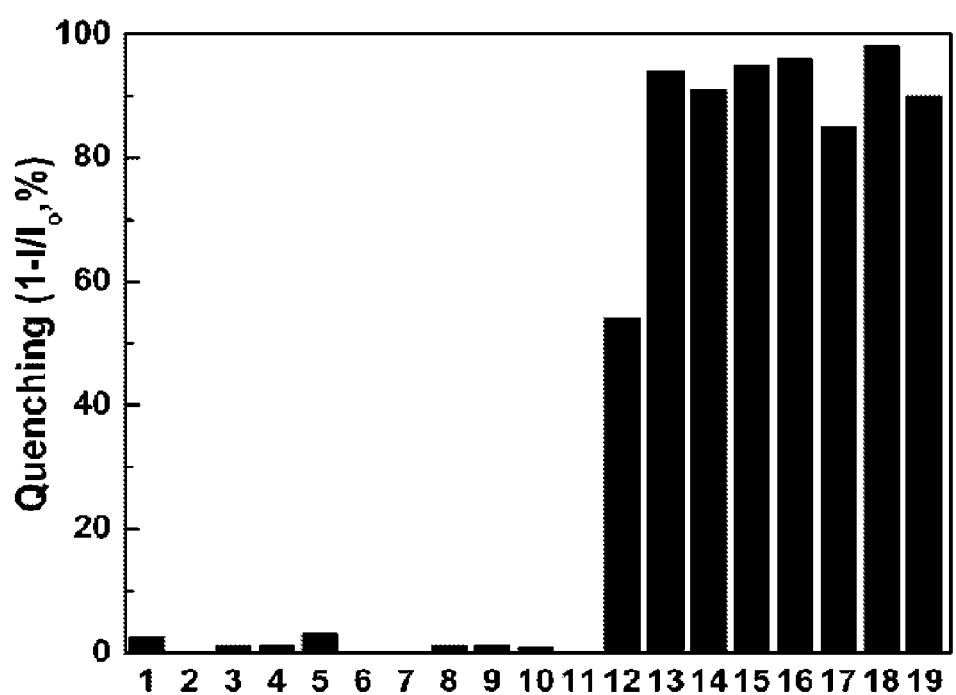
FIG. 9 is a bar graph of fluorescence response of the nanofibril film to various organic reagents: 1, methanol; 2, acetone; 3, acetic acid; 4, THF; 5, acetonitrile; 6, chloroform; 7, toluene; 8, hexane; 9, cyclohexane; 10, nitromethane; 11, nitrobenzene; 12, phenol; 13, cyclohexylamine; 14, dibutylamine; 15, aniline; 16, butylamine (3 s); 17, triethylamine; 18, hydrazine; 19, ammonium hydroxide. Unless otherwise marked, the exposure times for the amines and all the other reagents are 10 and 15 s, respectively.

The nanofibril film also demonstrated high selectivity in response to organic amines, with minimal fluorescence quenching observed for other common organic reagents, such as those listed in FIG. 9. For all the amines tested, more than 85% fluorescence quenching was observed for the nanofibril film upon exposure to the saturated vapor of amines, whereas all the other organic liquids and solids (except for phenol) examined as the potential background interference exhibited less than 3% fluorescence quenching under the same testing conditions (FIG. 9). The significant quenching (~54%) observed with phenol is likely due to its strong reducing power, i.e., electron-donating capability.

Figure 10:
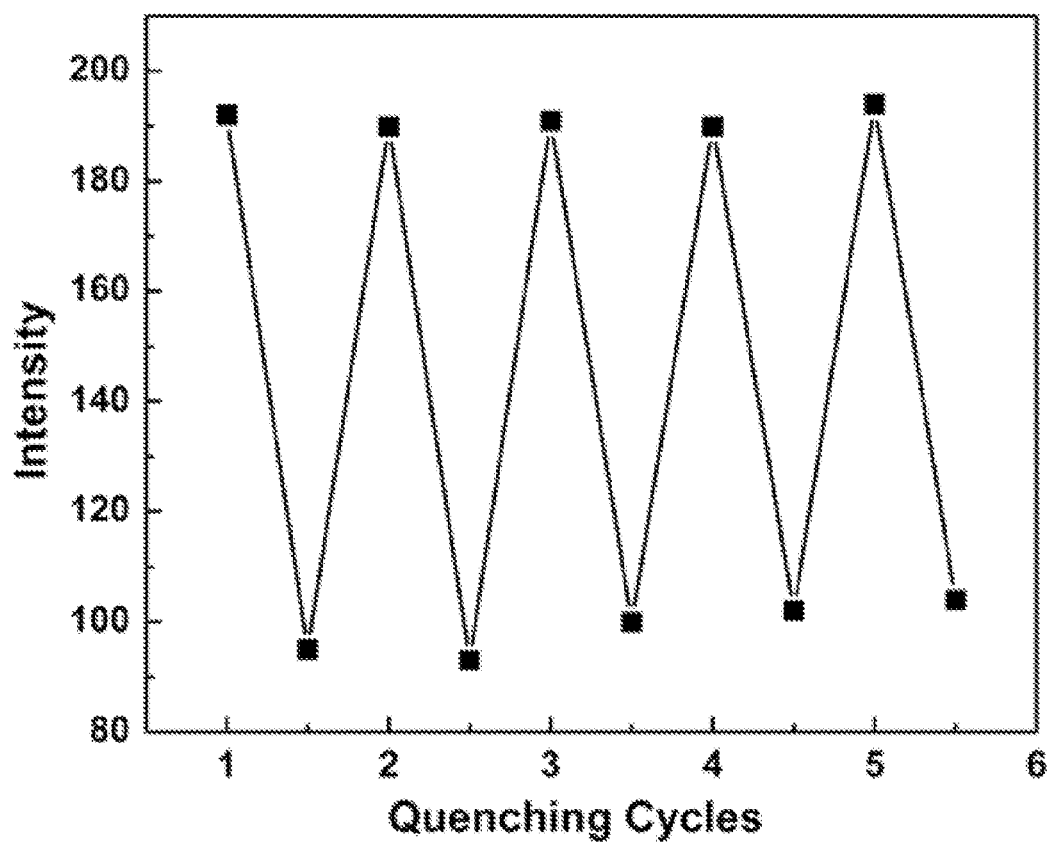
FIG. 10 shows five continuous cycles of quenching-recovery which were tested for a nanofibril film upon exposure to the saturated vapor of phenol (335 ppm). The quenching was performed by exposing the film to the phenol vapor for 15 s. After each cycle of quenching, the fluorescence of the film was recovered by exposing the film to an open air for 60 min or at an elevated temperature (60° C.) for 5 min.

Interestingly, the fluorescence quenching observed with phenol was highly reversible as shown in FIG. 10 (without chemical reaction), where the fluorescence of the nanofibril film after exposure to the phenol vapor could be recovered almost 100% simply by re-exposing it to atmosphere for ~60 min (or at an elevated temperature, e.g., 60° C., for only 5 min). The recovered film demonstrated the same quenching efficiency when used in the next cycle of the test with the phenol vapor (FIG. 10). Such a reversible quenching can be used to distinguish phenol (if present) from the organic amines, which otherwise exhibited almost irreversible fluorescence quenching under the same conditions, i.e., only ~50% of the fluorescence could be restored even after heating up the film overnight. The less reversibility observed for the quenching with amines is largely due to the much more stable chemical binding between amines and the anhydride moiety of molecule 1. Thus, the reported fluorescence sensor system can be typically provided as a single-use device, in the similar manner as a pH paper or pregnancy kit, which can be used by ordinary people without worrying about how to recover the materials after each use.

Although the fluorescence of the nanofibers cannot be recovered after exposed to the amines, the PTCDI materials (molecules) can be recovered simply by redissolving the nano fibers into chloroform, followed by appropriate purification (e.g., extraction with water) to remove the amines. The PTCDI molecules thus recovered (showing again the 100% fluorescence quantum yield) can be refabricated into the nano fibers and maintain the same sensing efficiency for amines. To this end, the PTCDI materials are recyclable, in contrast to the other irreversible sensor systems, for which the sensor materials are usually unrecyclable due to permanent chemical damage.

Example 2

This example provides a system with increased sensitivity for amines over Example 1 (lower detection limit). Ultrathin nanofibers only 30-50 nm in diameter were fabricated from a perylene based molecule, N-(1-hexylheptyl)perylene-3,4,9, 10-tetracarboxyl-3,4-anhydride-9,10-imide. The ultrathin nanofibers hereby fabricated, in comparison with the much larger fibers of Example 1 enables enhancement in fluorescence quenching efficiency, mainly due to the increased surface area offered by the ultrathin nano fibers, which in turn allows for increased vapor exposure to amines. Moreover, films formed from thinner fibers possess increase porosity, facilitating the expedient cross-film diffusion of gaseous species and thus enhancing the collection and accumulation of the trace vapor analytes, combination of which leads to unprecedented sensing sensitivity.

Figure 11:
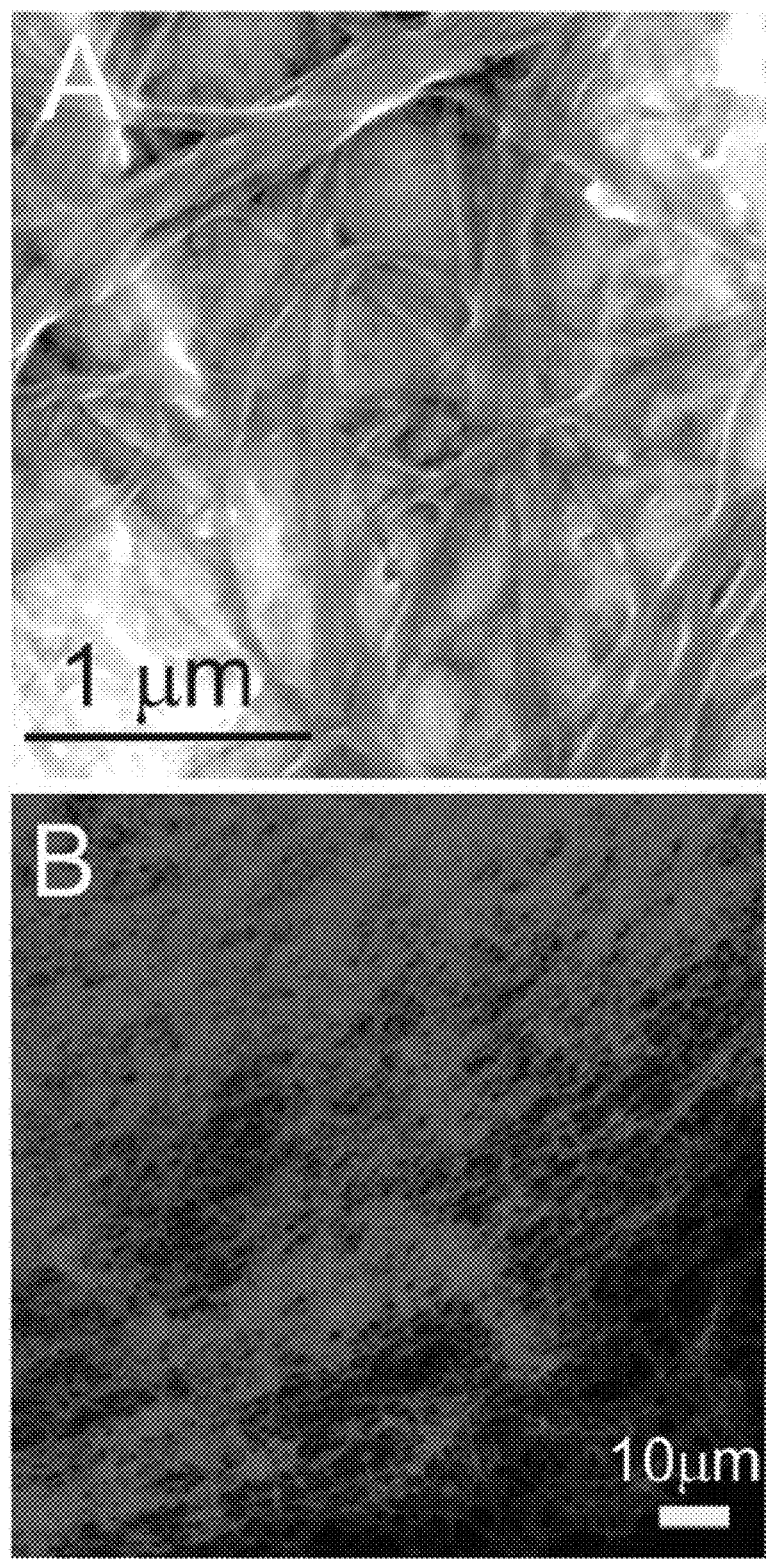
FIG. 11 (A) SEM image of the nanofibers deposited on a glass slide. (B) Fluorescence optical microscopy image of a nanofibril film deposited on a glass slide.

The ultrathin nanofibers were prepared by a quick crystallization process, i.e. directly injecting a good solvent solution of the perylene monoimide into a poor solvent in a small test tube, followed by aging. FIG. 11A shows a SEM image of the nanofibers measured by a FEI NanoNova microscope, demonstrating relatively uniform size and shape with diameter ranging from 30 to 50 nm. The nanofibers exhibit the same UV absorption and fluorescence emission spectra as that of the larger fibers (350 nm in diameter), which was fabricated through a vapor diffusion process, i.e. about 0.2 mL $CHCl_3$ solution of the perylene monoimide (1.7 mM) was exposed to a methanol vapor in a closed chamber for one day. The same spectral property (and thus electronic structure) is indicative of the same intermolecular organization for these two sizes of fibril structures despite of the different fabrication methods. This simplifies the comparative study when employing the two sizes of fibers for the vapor sensing of amines, for which the fiber size will be the only major factor determining the sensing sensitivity, rather than the molecular stacking mode. The same intermolecular stacking structure of the ultrathin nano fiber also yields the same fluorescence quantum yield as that of the larger fibers (ca. 15%), which facilitates the application in fluorescence sensing. FIG. 11B shows a fluorescence microscopy image of a nanofibril film deposited on a glass substrate, where strong red fluorescence emission of the nanofibers can easily be visually observed.

In this example, aniline was chosen as the target vapor analyte, mainly due to its relatively lower saturated vapor pressure (880 ppm) compared to other organic amines, which makes it easy to dilute the vapor down to a pressure level that matches the detection limit for the new nanofibril sensing system as described below. For example, 35 ppb of aniline vapor can be simply generated by injecting 0.2 mL saturated aniline vapor into a 5 mL cuvette. This value represents the lowest vapor pressure so far produced in this lab, and has been used in the test of the fluorescence quenching sensitivity of the ultrathin nanofibers. The fluorescence quenching experiments were performed by injecting the saturated aniline vapor into a sealed optical cell (5 mL) with the nanofibers deposited on one inner surface. The fluorescence spectra of such a nanofibril film (0.35 mg totally deposited) in the presence of different pressures of aniline vapor are shown in FIG. 12A.

Dramatic fluorescence quenching (13%) was observed for the nanofibril film after 60 s of exposure to only 35 ppb aniline vapor. As calculated, considering both the molecular amount of the nanofibers and aniline vapor, one aniline molecule can quench the fluorescence emission corresponding to seven building-block molecules within a nanofiber, i.e., the fluorescence quenching is amplified due to the one-dimensional enhancement of exciton diffusion along the long axis of nanofiber. Under the same measurement condition, only ca. 4% quenching (FIG. 13A) was observed with the larger nanofibers (350 nm in diameter), i.e. one aniline molecule can only quench two building-block molecules emission. The decreased quenching efficiency is likely due to the enlarged cross-section size of the fibers, for which the exciton diffusion is more bulk dispersed, not as confined along the long axis as expected for the ultrathin nano fibers. One-dimensional confined exciton diffusion is usually conducive to enhancement of fluorescence quenching if the intermolecular energy transfer is dominant along the long axis of nanofibers. This illustrates an effective way to improve the quenching (sensing) efficiency simply by decreasing the size of the nanofibers, which in turn increase the surface area of the nanofibril film thus deposited.

Figure 12:
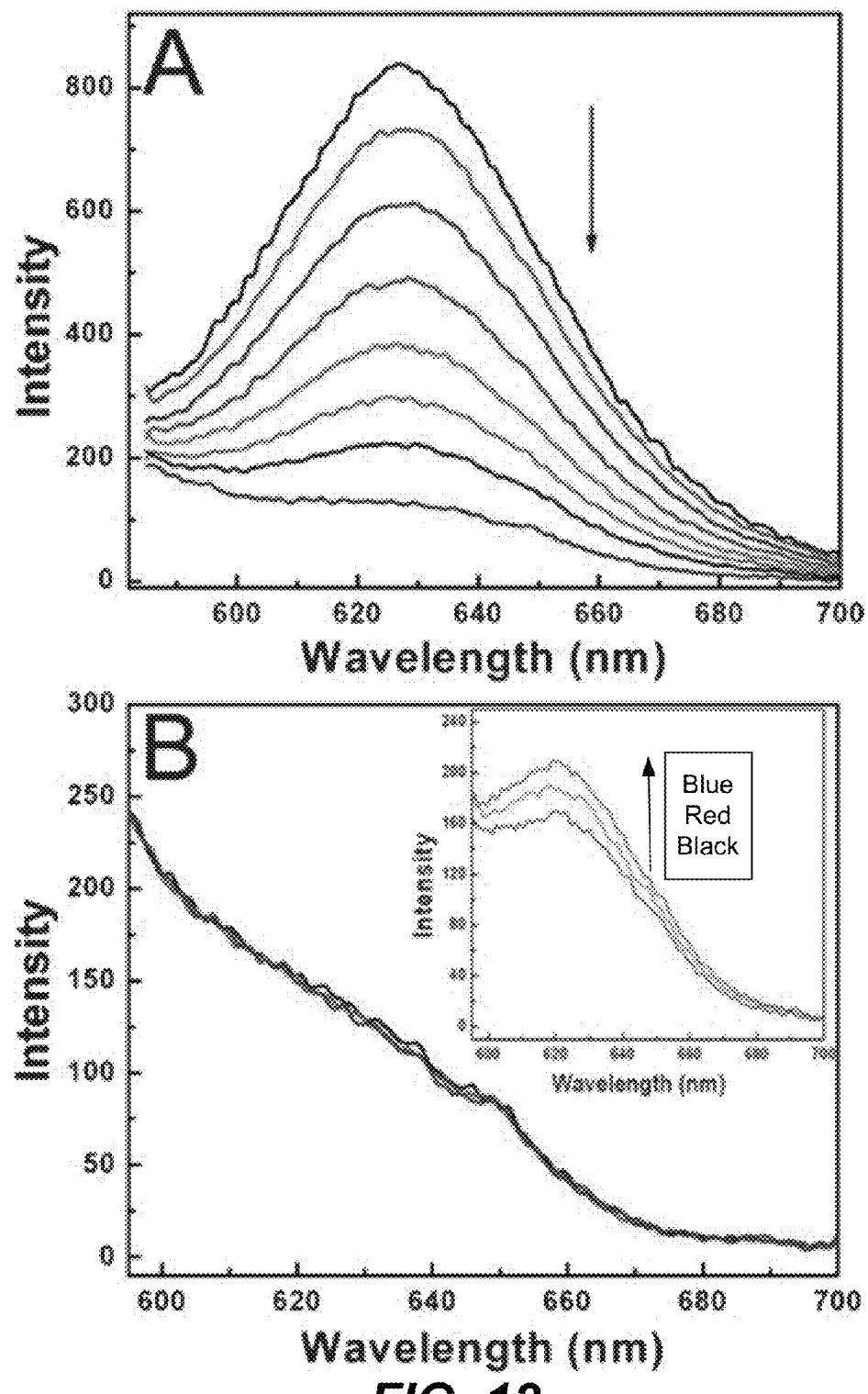
FIG. 12 (A) Fluorescence spectra of a nanofibril film after 60 s of exposure to aniline vapor at 35, 70, 175, 350, 525, 875, 1750 ppb. (B) Fluorescence spectra of a nanofibril film measured 15 min (red) and 30 min (blue) after the complete quenching (shown in black) in the presence of 1750 ppb aniline vapor. No spectral change with time indicates irreversibility of the quenching process. The same test was also performed with the larger fibers (350 nm in diameter) as shown in the inset, where significant recovery of the fluorescence emission was observed.

It should be noted that the real sensitivity of the nanofibril film shown in FIG. 12 should be much higher than the measured value if taking into account the technical fact that the small volume (0.2 µL) of aniline vapor cannot be released completely into the cuvette due to the significant absorption in the syringe. Moreover, the smaller size of nanofibers are conducive to enhancing the porosity of the film thus deposited, i.e., producing a smaller pore structure but with a more bulky inter-pore connection. This enhanced porosity, along with the increased surface area, not only facilitates the adsorption of amine vapor, but also strengthen the accumulation of the amine species thus collected from the gaseous phase.

Indeed, once the aniline molecules were adsorbed into the nanofibril film, they usually remain condensed within the solid phase, no release back to the gaseous atmosphere. This is consistent with the results presented in FIG. 12B, where the quenched fluorescence remained unchanged even 30 min after the film was exposed to 1750 ppb of aniline vapor. In contrast, for the film deposited from the larger fibers (diameter of 350 nm) the fluorescence intensity tended to gradually increase after exposure to the same vapor pressure of aniline, indicating significant release of aniline molecules back to the gaseous phase (inset, FIG. 12B). The sustainable accumulation of gaseous analytes within the film matrix is crucial for enabling trace vapor sensing, for which expedient and effective collection of analyte molecules from the atmosphere environment is often a defining factor for the sensing system.

Technically, as small as 0.1% (or below) change in fluorescence emission intensity can be detected by a well-calibrated photodetector (e.g., PMT). Based on such a photon detection threshold, one way to further improve the vapor sensing sensitivity (or detection limit) is to increase the signal-to-noise ratio. Generally, the less the nanofibers are employed, the less the quencher molecules are needed for the same percentage of fluorescence quenching, thereby leading to enhanced sensitivity to the trace vapor analyte. However, to maintain the sufficient adsorption and accumulation for the trace vapor, the film deposited from a smaller amount of fibers can maintain a sufficiently high surface area and porosity. To this end, ultrathin nanofibers are ideally suited for fabrication as thin films (potentially using much less materials), while still maintain high surface area and porosity.

Figure 13:
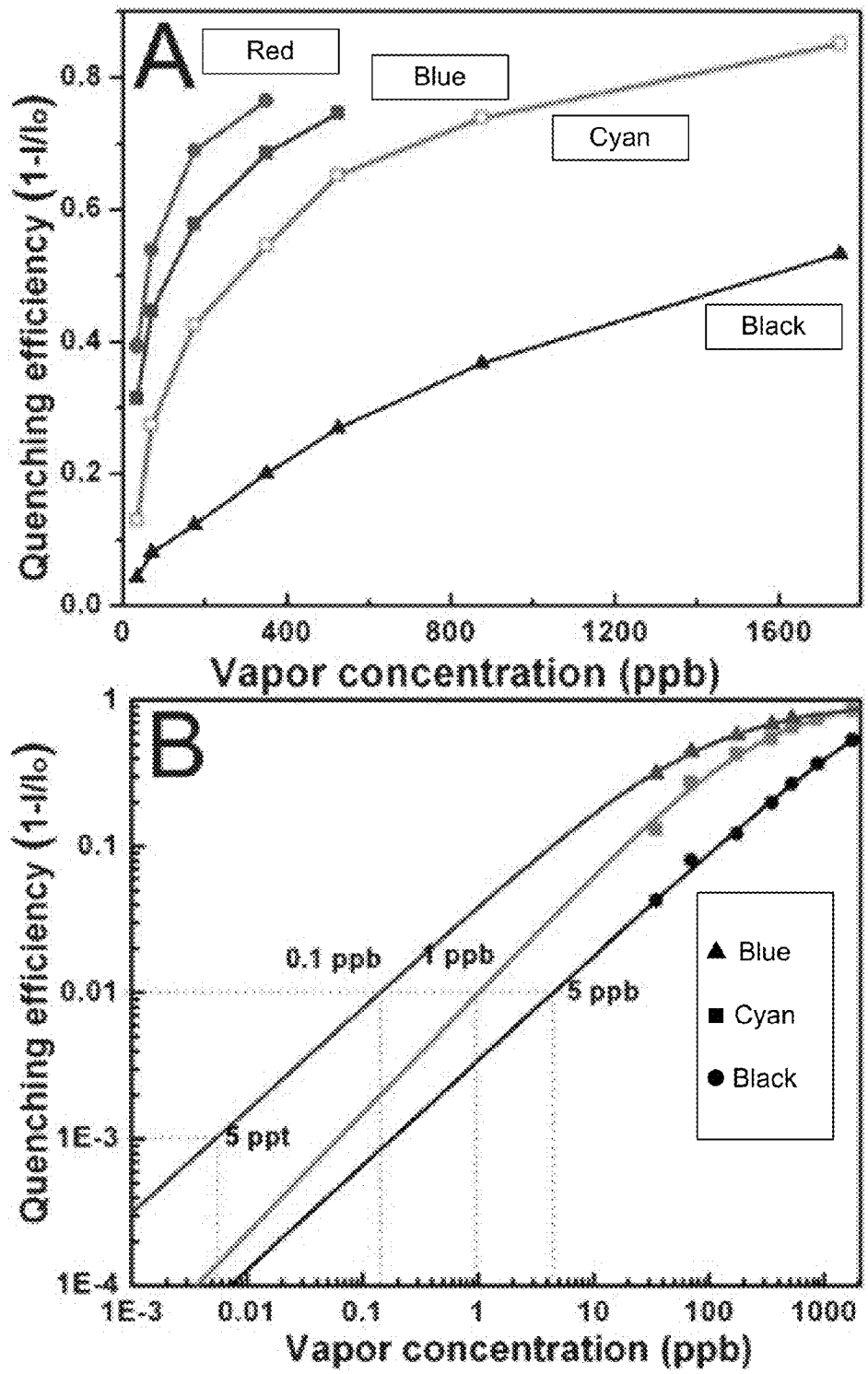
FIG. 13 (A) Fluorescence quenching efficiency ($1-I/I_0$) as a function of the vapor concentration aniline, measured for the nanofibril films deposited from both the ultrathin nano fibers (30-50 nm) and large fibers (350 nm); comparative investigation was performed on three different films fabricated from the ultrathin nanofibers using various amount of fibril materials (cyan: 0.35 mg; blue: 0.15 mg; red: 0.1 mg) as well as a film fabricated from the large fibers (black: 0.35 mg). (B) Fitting the three sets of data in (A) with the Langmuir equation aiming to predict the detection limit based on the common photon detection threshold of PMT. All data are with an error of ±3%.

FIG. 13A shows the fluorescence quenching in response to the vapor of aniline measured for the nanofibril films deposited from different amount of fibril materials. Under the same vapor pressure, larger quenching percentage was observed for the film fabricated with less amount of nanofibers. For example, under the vapor pressure of 35 ppb, 31% of fluorescence quenching was observed for the film deposited from 0.15 mg nanofibers, whereas only 13% of fluorescence quenching was obtained for the film deposited from 0.35 mg nano fibers. When decreasing the amount of nanofibers down to 0.1 mg, the quenching efficiency was further increased to 39% under the same condition. The increased quenching efficiency implies direct improvement of the detection limit.

FIG. 13B shows the fluorescence quenching data fitted with the Langmuir equation. Taking a fluorescence intensity change as 1%, the detection level for the 0.35 mg film is predicted at ca. 1 ppb, whereas for the 0.15 mg film the value could be as low as 0.1 ppb. In contrast, for the film deposited from 0.35 mg large fibers (350 nm diameter) the detection level is up to 5 ppb. The lower sensitivity thus observed for the large fibers is mainly due to the intrinsic smaller surface area and lower porosity. If assuming as small as 0.1% (or below) fluorescence quenching can be measured by a well-calibrated photodetector (e.g., PMT), the detection limit for the 0.15 mg film can be as low as ca. 5 ppt.

In conclusion, the fluorescence sensing sensitivity of perylene based nanofibril films for amine vapor was largely enhanced by decreasing the size of the nanofibers, which were fabricated through a solution-based self-assembly processing. The enhanced fluorescence sensing is mainly due to the increased surface area and the enhanced exciton diffusion along the long axis of nanofiber, along with the increased porosity intrinsic to the film deposited from the ultrathin nanofibers. The sensing efficiency (or detection limit) can further be enhanced by reducing the amount of the nanofibers employed in the film.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A nanofiber fluorescent sensor for detecting amines, the nanofiber fluorescent sensor comprising:
a porous film of entangled nanofibers, the nanofibers having a perylene stacked nanofiber structure consisting essentially of a single 3,4,9,10-tetracarboxyl perylene compound having the formula I:

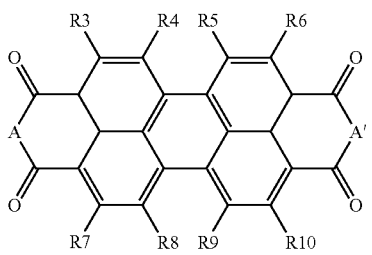

wherein (i) A' is O, thereby forming an anhydride as a first amine-binding moiety, and R1 and R3 through R10 are independently selected from the group consisting of amine-binding moieties, solubility enhancing groups, and hydrogen; or wherein (ii) A' is N—R2, and R1 through R10 are independently selected from the group consisting of amine-binding moieties, solubility enhancing groups, and hydrogen such that R1 through R10 include at least a second amine-binding moiety and a solubility enhancing group; and
a photodetector;
wherein the photodetector is configured to detect a change in fluorescence of the nanofiber structure upon exposure of the nanofiber structure to an amine.

2. The nanofiber fluorescent sensor of claim 1, wherein R1 is a C1 to C13 alkyl.

3. The nanofiber fluorescent sensor of claim 1, wherein R1 is hexylheptyl, pentylhexyl, or butylpentyl.

4. The fluorescent sensor of claim 1, wherein at least one of R1 and R2 is a C1 to C13 alkyl.

5. The fluorescent sensor of claim 1, wherein at least one of R1 and R2 is selected from the group consisting of hexylheptyl, pentylhexyl, butylpentyl, COOH, cyclopentyl, cyclohexyl, cycloheptyl, cyclooctyl, and cyclododecyl.

6. The fluorescent sensor of claim 1, wherein one or two of R3 through R10 are COOH.

7. The nanofiber fluorescent sensor of claim 1, wherein R4 and R5 collectively form maleic anhydride.

8. The nanofiber fluorescent sensor of claim 1, wherein the nanofiber structure has a diameter from about 10 nm to about 1000 nm.

9. The nanofiber fluorescent sensor of claim 1, wherein the nano fiber structure has a diameter from about 10 nm to about 50 nm.

10. The nanofiber fluorescent sensor of claim 1, wherein a fluorescence intensity of the nanofiber structure changes from 50% to 100% upon exposure of the nanofiber structure to compounds selected from the group consisting of phenol, cyclohexylamine, dibutylamine, aniline, butylamine, triethylamine, hydrazine, and ammonium hydroxide.

11. The nanofiber fluorescent sensor of claim 10, wherein the fluorescence intensity changes from about 80% to about 100% upon exposure of the nanofiber structure to each of cyclohexylamine, dibutylamine, aniline, butylamine, triethylamine, hydrazine, and ammonium hydroxide.

12. The nanofiber fluorescent sensor of claim 1, wherein the second amine-binding moiety includes an oxygen moiety or an acid.

13. The nanofiber fluorescent sensor of claim 12, wherein the second amine-binding moiety is a carboxylic acid.

14. The nanofiber fluorescent sensor of claim 1, wherein at least one of R3 through R10 is the second amine-binding moiety or the solubility enhancing group.

15. The nanofiber fluorescent sensor of claim 1, wherein (i) A' is O and R1 is a branched alkyl; or wherein (ii) A' is N—R2, the second amine-binding moiety is an anhydride or a carboxylic acid, and the solubility enhancing group is a branched alkyl.

16. The nanofiber fluorescent sensor of claim 1, wherein the sensor is capable of amine detection at ppb concentrations.

17. A method of detecting amines in a fluid, the method comprising:
a) exposing the nanofiber fluorescent sensor of claim 1 to a fluid sample; and
b) displaying a fluorescence change upon exposure of the nanofiber fluorescent sensor to the fluid sample.

18. The method of claim 17, wherein the porous film of nanofibers is not substantially soluble in the fluid sample.

19. The method of claim 18, further comprising regenerating the nanofiber fluorescent sensor by dissolving the porous film of entangled nanofibers and regenerating nanofibers.

20. The method of claim 17, wherein the photodetector can measure fluorescence emission intensity.

21. The method of claim 17, wherein the displaying is a quantitative measure of fluorescence intensity change.

22. The method of claim 17, wherein the displaying is qualitative.

23. A method of making a nanofiber fluorescent sensor, the method comprising
a) synthesizing a single 3,4,9,10-tetracarboxyl perylene compound having the formula I:

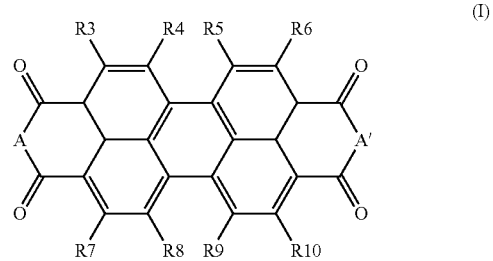

wherein (i) A' is O, thereby forming an anhydride as a first amine-binding moiety, and R1 and R3 through R10 are independently selected from the group consisting of amine-binding moieties, solubility enhancing groups, and hydrogen; or wherein (ii) A' is N—R2, and R1 through R10 are independently selected from the group consisting of amine-binding moieties, solubility enhancing groups, and hydrogen such that R1 through R10 include at least a second amine-binding moiety and a solubility enhancing group; and b) self-assembling the single perylene compound into a porous film of entangled nanofibers, the nanofibers having a perylene stacked nanofiber structure consisting essentially of the single perylene compound, wherein the self-assembing is done via a process selected from the group consisting of a slow controlled solvent-exchange step, rapid solution dispersion, phase transfer at an interface between two solvents, sol-gel processing, and a surface assisted process; and c) operably connecting a photodetector to the nanofibers; wherein the photodetector is configured to detect a change in fluorescence of the nanofiber structure upon exposure of the nanofiber structure to an amine.

* * * * *